US008911089B2

(12) United States Patent
Kim et al.

(10) Patent No.: US 8,911,089 B2
(45) Date of Patent: Dec. 16, 2014

(54) NORMALIZATION OF RETINAL NERVE FIBER LAYER THICKNESS MEASUREMENTS MADE BY TIME DOMAIN-OPTICAL COHERENCE TOMOGRAPHY

(75) Inventors: Jong S. Kim, Pittsburgh, PA (US); Hiroshi Ishikawa, Pittsburgh, PA (US); Joel S. Schuman, Pittsburgh, PA (US); Gadi Wollstein, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 388 days.

(21) Appl. No.: 13/510,732

(22) PCT Filed: Nov. 19, 2010

(86) PCT No.: PCT/US2010/057402
§ 371 (c)(1),
(2), (4) Date: Dec. 11, 2012

(87) PCT Pub. No.: WO2011/063220
PCT Pub. Date: May 26, 2011

(65) Prior Publication Data
US 2013/0077046 A1 Mar. 28, 2013

Related U.S. Application Data

(60) Provisional application No. 61/263,036, filed on Nov. 20, 2009.

(51) Int. Cl.
| *A61B 3/14* | (2006.01) |
| *A61B 3/00* | (2006.01) |
| *A61B 3/10* | (2006.01) |
| *G01B 9/02* | (2006.01) |
| *G01B 11/06* | (2006.01) |

(52) U.S. Cl.
CPC ............ *A61B 3/102* (2013.01); *G01B 9/02087* (2013.01); *G01B 2290/65* (2013.01); *G01B 9/02091* (2013.01); *G01B 9/02027* (2013.01); *G01B 11/06* (2013.01)
USPC ......................................... 351/206; 351/246

(58) Field of Classification Search
USPC ......... 351/200, 206, 205, 212, 222, 245, 246; 600/383, 452, 425
See application file for complete search history.

(56) References Cited

U.S. PATENT DOCUMENTS

| 7,139,602 B2 | 11/2006 | Essock et al. |
| 7,347,548 B2 | 3/2008 | Huang et al. |

(Continued)

OTHER PUBLICATIONS

International Search Report PCT/US2010/057402 dated Aug. 19, 2011.

(Continued)

*Primary Examiner* — William Choi
*Assistant Examiner* — Brandi Thomas
(74) *Attorney, Agent, or Firm* — Foley & Lardner LLP

(57) ABSTRACT

A scan location matching (SLM) method identifies conventional time domain optical coherence tomography (TD-OCT) circle scan locations within three-dimensional spectral domain OCT scan volumes. A technique uses both the SLM algorithm and a mathematical retinal nerve fiber bundle distribution (RNFBD) model, which is a simplified version of the anatomical retinal axon bundle distribution pattern, to normalize TD-OCT thickness measurements for the retinal nerve fiber layer (RNFL) of an off-centered TD-OCT circle scan to a virtual location, centered on the optic nerve head. The RNFBD model eliminates scan-to-scan RNFL thickness measurement variation caused by manual placement of TD-OCT circle scan.

2 Claims, 11 Drawing Sheets

(56) References Cited

U.S. PATENT DOCUMENTS

| | | | |
|---|---|---|---|
| 7,798,647 B2 * | 9/2010 | Meyer et al. | 351/246 |
| 2009/0073387 A1 | 3/2009 | Meyer et al. | |

OTHER PUBLICATIONS

Argyrios Tzamalis et al., "Improved reproducibility of retinal nerve fiber layer thickness measurements with the repeat-scan protocol using the Stratus OCT in normal and glaucomatous eyes", Graefes Arch Clin Exp Ophthalmol, 2009, 247, pp. 245-252.

Cyl Cheung et al., "Effects of scan circle displacement in optical coherence tomography retinal nerve fibre layer thickness measurement: a RNFL modelling study", Eye, 2009, 23, pp. 1436-1441.

David Huang et al., "Optical Coherence Tomography", Science, 1991, vol. 254, pp. 1178-1181.

Drexler Wolfgang et al., "State-of-the-art retinal optical coherence tomography", Progress in Retinal and Eye Research, 27, 2008, pp. 45-88.

F Grehn et al., "Glaucoma", Essentials in Ophthalmology Series, Springer, Berlin Heidelber New York, 2004.

Gadi Wollstein et al., "Optical Coherence Tomography Longitudinal Evaluation of Retinal Nerve Fiber Layer Thickness in Glaucoma", Arch Ophthalmol, vol. 123, Apr. 2005, pp. 464-470.

J S Kim et al., "Retinal nerve fibre layer thickness measurement reproducibility improved with spectral domain optical coherence tomography", Br J Ophthalmol, 2009, 93, pp. 1057-1063.

Joel S. Schuman et al., "Optical Coherence Tomography: A new tool for glaucoma diagnosis", Current opinion in Ophthalmology, 1995, 6,11, pp. 89-95.

Joel S. Schuman et al., Quantification of Nerve Fiber Layer Thickness in Normal and Glaucomatous Eyes Using Optical Coherence Tomography, Arch Ophthalmol, vol. 113, May 1995, pp. 586-596.

Jong S. Kim et al., "Retinal Nerve Fiber Layer Thickness Measurement Comparability between Time Domain optical Coherence Tomography (OCT) and Spectral Domain OCT", Invents Ophthalmo Vis Sci, 2010, 51, pp. 896-902.

Kendall E. Atkinson, "An Introduction to Numerical Analysis", Second Edition, John Wiley & Sons Inc, 1989.

Lanning B Kline et al., "Optical Nerve Disorders", 2nd Edition, Ophthalmology Monograph 10, The American Academy of Ophthalmology, pp. 1-8.

Maciej Wojtkowski et al., "Ophthalmic Imaging by Spectral Optical Coherence Tomography", Am J Ophthalmol, 2004, 138, pp. 412-419.

Maciej Wojtkowski et al., "Three-dimensional Retinal Imaging with High-Speed Ultrahigh-Resolution Optical Coherence Tomography", Ophthalmology, 2005, pp. 1734-1746.

Michelle L. Gabriele et al., "Optical Coherence Tomography Scan Circle Location and Mean Retinal Nerve Fiber Layer Measurement Variability", Investigative Ophthalmology & Visual Science, Jun. 2008, vol. 49, No. 6. pp. 2315-2321.

Tarkan Mumcuoglu et al., "Improved Visualization of Glaucomatous Retinal Damage Using High-Speed Ultrahigh-Resolution Optical Coherence Tomography", Ophthalmology, 2008, 115, pp. 782-789.

Vivek J. Srinivasan et al., "Ultrahigh-Speed optical Coherence Tomography for Three-Dimensional and En Face Imaging of the Retina and Optic Nerve Head", Investigative Ophthalmology & Visual Science, Nov. 2008, vol. 49, No. 11, pp. 5103-5110.

* cited by examiner

NORMALIZATION OF RETINAL NERVE FIBER LAYER THICKNESS MEASUREMENTS MADE BY TIME DOMAIN-OPTICAL COHERENCE TOMOGRAPHY

CROSS-REFERENCE TO RELATED PATENT APPLICATIONS

This application claims priority to U.S. provisional application No. 61/263,036, filed Nov. 20, 2009, the entire contents of which are incorporated herein by reference.

STATEMENT REGARDING FEDERALLY SPONSORED RESEARCH

This invention was made with United States government support in part under grant numbers R01-EY13178-09, R01-EY11289-23, and P30-EY08098-20, awarded by the National Institutes of Health (Bethesda, Md.), The Eye and Ear Foundation (Pittsburgh, Pa.), and unrestricted grants from Research to Prevent Blindness, Inc. (New York, N.Y.). The United States government has certain rights in the invention.

BACKGROUND OF THE INVENTION

Glaucoma is a progressive optic neuropathy, which induces irreversible structural damage of the retina that is manifested, for example, in retinal ganglion cell loss and thinning, due to axon loss, of the retinal nerve fiber layer (RNFL).[1,2] Glaucomatous damage occurs along axon bundle and creates a localized, wedge-shaped RNFL defect, evident in a red-free fundus photograph (FIG. 1) because axons are originated from the retinal ganglion cells and converge at the optical nerve head (ONH).[1,2] The cross-sectional tissue structure of the retina can be revealed by using optical coherence tomography (OCT), which is a non-contact and non-invasive imaging modality.[3] The conventional time domain-OCT, 3.4-mm diameter circle scan, centered on the ONH (FIG. 2), enables quantitative RNFL analysis.[4,5] Furthermore, multiple repeated RNFL thickness measurements, made using TD-OCT circle scans in different time points, also provide a useful approach to detecting glaucoma progression, earlier than visual field (VF) reduction.[6]

One limitation of TD-OCT circle scan is measurement variability in long term follow-up because operator manually places the TD-OCT circle scan around the ONH (FIG. 3).[7,8] There is a method, called "Repeat-scan function," implemented via Stratus OCT system software (CZMI). With this function, an operator is able to place the TD-OCT circle scan with a unique landmark at the base-line (first visit) scan, in order that the same scan at the second visit can be performed on, the same location. The improvement thus achieved is small, i.e., there is significant improvement but only in temporal quadrant, due to the difficulty of registration.[9]

Spectral domain OCT (SD-OCT) technology, with faster scanning speed and higher axial resolution relative to the conventional TD-OCT, has allowed three-dimensional (3D) volume sampling by raster scanning in the region of interest.[10-13] An SD-OCT fundus image, which can be obtained by summing the back scattered signal at each transverse point of a retinal raster scan, visualizes especially the presence of horizontal eye motion during SD-OCT scanning, because the discontinuities of retinal blood vessels appearing on SD-OCT fundus image are generated by saccadic eye motion.[11-13] 3D SD-OCT volume data also enable a virtual OCT cross-sectional (B-scan) image along any sampling line (curved or straight). For example, TD-OCT circle scan can be virtually performed within 3D SD-OCT volume (FIG. 4D, circle). The virtually sampled B-scan after near perfect registration can be used for comparison between TD-OCT and SD-OCT.[14] In addition, a two-dimensional (2D) RNFL thickness map (FIG. 4C) can be created by segmenting RNFL on each B-scan of 3D SD-OCT volume scan.[15]

SUMMARY OF THE INVENTION

The present invention makes possible the normalization of RNFL thickness measurements of an off-centered TD-OCT circle scan to a virtual location, centered on the ONH, by using both a mathematical model of the retinal tissue pattern and scan location matching algorithm.[14] Once one normalizes the RNFL thickness measurements of TD-OCT circle scan, pursuant to the invention, clinicians can track, compare, and finally detect any abnormal retinal change over a long period of time, without RNFL thickness-measurement variability caused by the off-centered TD-OCT scans.

To these ends, therefore, the invention provides a method for normalizing thickness measurements of a retinal nerve fiber layer in a two-dimensional optical coherence tomography image and a three-dimensional optical coherence tomography image, each image containing that layer. The inventive method comprises the steps of:

(A) performing at least one circle scan in said two-dimensional image to obtain a thickness of said layer;

(B) establishing image registration between the two-dimensional image and the three-dimensional image;

(C) generating a two-dimensional thickness map of the thickness of the layer from the three-dimensional image;

(D) performing at least three concentric circle scans for each of the superior hemi-sphere and the inferior hemi-sphere of the layer in the two-dimensional thickness map to delineate space coordinates of a center of gravity of the thickness in each respective hemi-sphere;

(E) generating at least one polynomial function based on the space coordinates of the respective centers of gravity to create a plurality of fitting curves; and (F) performing a mathematic interpolation of the plurality to obtain thickness measurements along a virtual path in the two-dimensional thickness map, whereby the thickness measurements of said layer are normalized along the virtual path.

In one embodiment of the invention, the aforementioned polynomial function is a second order polynomial function.

Illustration of Inventive Methodology

Twelve healthy subjects (12 eyes) and seven glaucoma subjects (7 eyes) were recruited from the University of Pittsburgh Medical Center (UPMC) Eye Center. University of Pittsburgh Institutional Review Board and ethics committee approval were obtained for the study, and informed consent was obtained from all subjects. This study followed the tenets of the Declaration of Helsinki and was conducted in compliance with the Health Insurance Portability and Accountability Act.

Clinical Diagnosis

Inclusion criteria were best corrected visual acuity ≥20/40, refractive error within ±6.0 D, and no media opacities that interfere with TD-OCT video fundus imaging. Subjects were excluded if they had any previous intra-ocular surgeries other than uneventful cataract extraction. Subjects also were excluded if they were using medications known to affect retinal thickness or if they had systemic diseases that might affect the retina or visual field. One randomly selected eye was included if both eyes were eligible in the same subject.

Healthy eyes had normal comprehensive ocular examination and automated perimetry glaucoma hemifield test (GHT, standard 24-2 SITA) within normal limits (Humphrey Visual Field Analyzer, HVF III, Carl Zeiss Meditec, Inc. (CZMI), Dublin, Calif.). Glaucomatous eyes showed both glaucomatous optic neuropathy and GHT outside normal limits. Glaucomatous optic neuropathy was defined as general or focal neuro-retinal rim thinning, disc hemorrhage or inter-eye cup/disc ratio asymmetry >0.2.

Image Acquisition

For this study, the peripapillary region was scanned on all eyes using TD-OCT (Stratus OCT; CZMI) and SD-OCT (Cirrus HD-OCT; CZMI) at a single visit. All subject eyes had dilated pupils at the time of OCT scan.

TD-OCT

The Circle scan protocol of Stratus OCT (system software version 5.0) was used to obtain cross-sectional images around the ONH. The Circle scan was a single 3.4 mm diameter circular scan with 256×1024 samplings. Each eye had nine Circle scans in a single session by one operator. Each of nine circle scans was systematically displaced by the same operator so that each circle scan had clearly visible displacement without touching the ONH margin appeared on the Stratus OCT video fundus photo (FIG. 5). Signal strength (SS) had to be six or above as the manufacturer recommends. Consecutive 5% or cumulative 10% segmentation failure (i.e., obvious deviation of the segmented inner and/or outer RNFL borders from the subjectively perceived borders) within a given image was considered to be poor analysis quality and discarded.

SD-OCT

A single 3D SD-OCT volume scan manually centered on the ONH was performed by using "Optic Disc Cube 200× 200" scan protocol from each eye (FIG. 4). This volume scan had equally spaced sampling points (A-scans) in X- and Y-plane (i.e., isotropic raster scan contained 200×200×1024 samplings of a 6×6×2 mm volume) and was acquired in 1.48 seconds. Scan quality was assessed by using signal strength (SS). Poor quality scans had SS less than 8 and were discarded, as the manufacturer recommends. Images with horizontal eye movements during scanning observed as more than the diameter of major vessels on SD-OCT fundus (en face) images were excluded from this study. ONH margin was detected and then RNFL thickness was measured on every sampling point, except for the area within the ONH, in a fully automated fashion using a software program of our own design. The volume scans with more than 10% of frames labeled as RNFL analysis failure were considered as poor quality scans and discarded. The segmentation failure criteria for virtual OCT slices (or re-sampled images) from the SD-OCT scans was the same as for the TD-OCT scans.

Mathematical Axon Bundle Distribution (ABD) Mapping and Normalization of RNFL Thickness Measurements RNFL thickness measurements normalization was achieved by utilizing the fact that RNFL thickness decreases along the anatomical RNFBD.[8] Knowing the TD-OCT scan location within the corresponding 3D SD-OCT volume data allows us to adjust RNFL thickness measured on an off-centered circle by tracking the RNFBD to the corresponding point on the virtually centered circle. The decay along the RNFBD was assumed to be the same in both time points when TD- and SD-OCT scans were obtained. The detailed flow chart of the normalization is shown in FIG. 6.

RNFBD map was generated by interpolating the major RNFBD curvatures, one in the superior and another in the inferior hemifield (FIG. 7C), mimicking the anatomical RNFBD (FIG. 8A). Major RNFBD was detected in each hemifield by detecting the center of gravity of the RNFL thickness on multiple resampled RNFL profiles along concentric circles with the diameter ranging from 3.0 to 5.4 mm, with 0.015 mm interval centered on the ONH (FIGS. 7C, D, and E). The "raw" major RNFBD information was smoothed by fitting two different curvature models: quadratic ($f_Q(x)=ax^2+bx+c$) and linear ($f_L(x)=ax+b$) curves (FIGS. 8B and C).[16] The major RNFBD curvature models, $f_Q(x)$ and $f_L(x)$, from superior and inferior hemispheres (FIG. 7E) then were linearly interpolated, p(x), along concentric circles with a 0.015 mm interval centered on the ONH.[16]

$$p(x)=f(x_i)+(f(x_{i+1})-f(x_i))\times(x-x_i)/(x_{i+1}-x_i)$$

The interpolation of RNFBD curvature was performed only outside the ONH region. In addition, the interpolated lines (FIGS. 8B and C) were not always quadratic or linear functions because the center of concentric circle was the ONH center instead of the intersection point of the two major RNFBD curvature models (i.e., superior and inferior hemispheres). This was why the individual line on FIG. 8C does not always look like a linear (i.e., quasi-linear) function.

By using the proposed SLM method, the TD-OCT scan location was identified within the 3D SD-OCT data (FIG. 9C). Then corresponding points along the virtual centered circle on the SD-OCT data were traced for each sampling point on the off-centered TD-OCT circular scan along the RNFBD map (FIGS. 9F and G). The RNFL thickness ratio ($R_U$) on these corresponding points (i.e., a/b=a*/b* as in FIGS. 9F and G) was then applied to compute the normalized RNFL thickness at each sampling point. The TD-OCT RNFL thickness normalization equation is:

$$b(x,y)=a(x,y)\times Ru,$$

$$Ru=a^*(x,y)/b^*(x,y),$$

Ru: RNFL thickness ratio
a(x, y): RNFL thickness of the off-centered TD-OCT circle scan,
b(x, y): Normalized RNFL thickness at the virtual location on TD-OCT scale,
a*(x, y): RNFL thickness at the matched SD-OCT circle scan (SD-OCT scale),
b*(x, y): RNFL thickness at the ONH centered SD-OCT circle scan,
x, y: X-Y coordinate on the SD-OCT fundus image.

Normalization Performance Assessment

The performance of the RNFL thickness normalization method was assessed by comparing the reproducibility of the global and sectoral RNFL thickness measurements of the following methods: 1) the actual TD-OCT scan with one centered and eight off-centered locations, 2) the quadratic RNFBD normalization method (QM), and 3) the quasi-linear RNFBD normalization method (QLM). The difference between the QM and QLM was the stiffness of estimated RNFBD curves (FIGS. 7B and C).

Statistical Analysis

The reproducibility of the methods was assessed by a structural equation model for the measurement error. This statistical model assessed bias and imprecision simultaneously using maximum likelihood estimates of the model parameters along with their corresponding 95% confidence intervals (CI) and p-values.

Results

Subject demographics were summarized in Table 1. The average RNFL thickness measurement from TD-OCT scans was 104.0 µm (±9.0 µm) with 12 healthy eyes and 91.5 µm (±16.3 µm) with 7 glaucomatous eyes (Table 2). No scans were excluded due to either eye motion and/or poor signal level, and subjectively there was neither SLM algorithm nor RNFBD mapping failure.

TABLE 1

Patient Demographics

| | Normal | Glaucoma |
|---|---|---|
| Number of patients | 12 | 7 |
| Mean (±SD) age (years) | 35.2 (±11.7) | 63.2 (±4.3) |
| Gender | Male: 5, Female: 7 | Male: 2, Female: 5 |

TABLE 2

The RNFL thickness measurements.

| Sector | | Healthy | Glaucoma |
|---|---|---|---|
| Global Mean | | 104.0 ± 9.0 | 91.5 ± 16.3 |
| Quadrant | Temporal | 70.5 ± 24.0 | 70.8 ± 13.6 |
| | Superior | 118.7 ± 28.1 | 104 ± 13.7 |
| | Nasal | 93.9 ± 33 | 85.3 ± 27.1 |
| | Inferior | 132.9 ± 21.8 | 106 ± 37.2 |
| Clock Hour | 1 | 56.7 ± 23.6 | 61.1 ± 12.2 |
| | 2 | 83.6 ± 32.1 | 79.4 ± 21 |

Table 3 shows the statistical analysis results of structural equation model. The reproducibility of RNFL thickness measurement between the three different methods (TD-OCT scan, QM, and QLM) was compared. When a ratio is equal to one, the reproducibilities are identical. For example, the estimated reproducibility ratio (QLM/TD-OCT) of global mean RNFL thickness measurements was 0.80 (95% CI 0.63 to 1.02), which indicates that the reproducibility of QLM was 20% better (i.e., the variance was smaller) than for TD-OCT. Yet, the reproducibilities are not statistically significantly different because the 95% CI includes one. The reproducibility ratios showed that quadratic RNFBD normalization approach statistically significantly improved RNFL thickness measurement reproducibility in comparison with TD-OCT for all sectors except for global mean, nasal quadrant, and clock hour 11. For quasi-linear RNFBD normalization method, the reproducibility ratios were statistically significant in all sectors except global mean. In addition, the variability of normalized RNFL measurement was close to the previously reported TD- and SD-OCT reproducibility on a different population (FIG. 10, dark solid).[17]

TABLE 3

The imprecisio SD [95% CI] comparison. When the imprecision SD ratio is equal to one, the reproducibilities of RNFL thickness measurement are identical.

| | | TD-OCT Imprecision SD (μm) (A) | Quadratic RNFBD Mapping | | | Quasi-linear RNFBD Mapping | | |
|---|---|---|---|---|---|---|---|---|
| Sector | | | $\beta_{QUAD}/\beta_{TD-OCT}$ | Imprecision SD (μm) (B) | Imprecision SD ratio (B/A) | $\beta_{QUASI}/\beta_{TD-OCT}$ | Imprecision SD (μm) (C) | Imprecision SD ratio (C/A) |
| Global Mean | | 4.55 [5.31-6.31] | 1.03 [0.90-1.17] | 4.42 | 0.83 [0.64-1.08] | 0.98 [0.89-1.07] | 4.23 | 0.80 [0.63-1.02] |
| Quadrant | Temporal | 19.86 [17.24-23.18] | 1.11 [0.81-1.52] | 7.40 | 0.37 [0.25-0.54] | 1.01 [0.89-1.14] | 6.21 | 0.31 [0.24-0.40] |
| | Superior | 19.61 [16.79-23.16] | 1.07 [0.74-1.49] | 9.50 | 0.48 [0.32-0.76] | 1.05 [0.90-1.23] | 10.07 | 0.51 [0.39-0.68] |
| | Nasal | 24.62 [21.07-29.25] | 0.71 [0.26-1.78] | 10.92 | 0.44 [0.16-1.25] | 1.07 [0.88-1.30] | 7.48 | 0.30 [0.23-0.41] |
| | Inferior | 19.64 [17.05-22.93] | 1.04 [0.87-1.28] | 9.15 | 0.47 [0.35-0.62] | 0.94 [0.84-1.04] | 8.00 | 0.41 [0.32-0.52] |
| Clock Hour | 1 | 27.21 [23.30-32.34] | 0.88 [0.53-1.32] | 11.79 | 0.43 [0.26-0.75] | 1.02 [0.83-1.21] | 16.60 | 0.61 [0.46-0.82] |
| | 2 | 26.87 [23.02-31.94] | 0.56 [0.13-1.18] | 21.80 | 0.81 [0.35-3.39] | 1.01 [0.77-1.28] | 11.44 | 0.43 [0.31-0.60] |
| | 3 | 24.91 [21.46-29.12] | 0.90 [0.43-1.69] | 11.21 | 0.45 [0.23-0.99] | 0.94 [0.68-1.27] | 11.98 | 0.48 [0.33-0.72] |
| | 4 | 25.93 [22.39-30.27] | 1.15 [0.67-1.86] | 9.38 | 0.36 [0.21-0.66] | 0.91 [0.76-1.10] | 10.35 | 0.40 [0.30-0.53] |
| | 5 | 30.01 [25.96-35.05] | 0.94 [0.63-1.35] | 11.23 | 0.37 [0.24-0.59] | 1.04 [0.89-1.22] | 10.31 | 0.34 [0.26-0.45] |
| | 6 | 35.63 [30.51-42.31] | 0.90 [0.55-1.42] | 13.27 | 0.37 [0.22-0.65] | 1.03 [0.90-1.17] | 10.23 | 0.29 [0.22-0.37] |
| | 7 | 22.05 [18.88-25.77] | 1.45 [1.16-1.76] | 9.38 | 0.43 [0.32-0.59] | 0.95 [0.86-1.05] | 14.21 | 0.64 [0.51-0.83] |
| | 8 | 27.28 [23.37-32.31] | 1.03 [0.70-1.46] | 10.83 | 0.40 [0.26-0.63] | 1.03 [0.91-1.17] | 10.70 | 0.39 [0.30-0.51] |
| | 9 | 15.50 [13.27-18.30] | 1.30 [0.72-2.18] | 7.14 | 0.46 [0.25-0.88] | 0.95 [0.77-1.18] | 9.43 | 0.61 [0.45-0.83] |
| | 10 | 25.45 [22.04-29.70] | 1.68 [1.12-2.46] | 6.52 | 0.26 [0.16-0.41] | 0.94 [0.83-1.06] | 12.86 | 0.51 [0.40-0.65] |
| | 11 | 21.35 [18.29-25.38] | 1.07 [0.65-1.56] | 12.54 | 0.59 [0.36-1.01] | 0.97 [0.83-1.13] | 12.81 | 0.60 [0.46-0.79] |
| | 12 | 30.17 [25.84-35.81] | 1.03 [0.63-1.63] | 11.25 | 0.37 [0.22-0.65] | 1.02 [0.87-1.18] | 12.80 | 0.42 [0.32-0.56] |

TABLE 2-continued

The RNFL thickness measurements.

| Sector | Healthy | Glaucoma |
|---|---|---|
| 3 | 117.6 ± 31.9 | 116.8 ± 27.8 |
| 4 | 123 ± 40.3 | 102.4 ± 20.8 |
| 5 | 115.2 ± 36.8 | 93 ± 17.5 |
| 6 | 105.1 ± 30.4 | 96.3 ± 19.6 |
| 7 | 83.7 ± 33.7 | 79 ± 29.4 |
| 8 | 93.7 ± 38.2 | 80.5 ± 37.9 |
| 9 | 110.1 ± 32.2 | 101.3 ± 48.8 |
| 10 | 144.3 ± 33.5 | 111.3 ± 41.8 |
| 11 | 144.9 ± 34.8 | 105.7 ± 48.3 |
| 12 | 80.2 ± 22.9 | 77.9 ± 26.8 |

The present inventors thus have developed and evaluated an automated algorithm to normalize the RNFL thickness measurement of off-centered TD-OCT circle scan to a virtual properly centered location. The results show that the mathematical RNFBD model, in accordance with the invention, properly identified the anatomical RNFBD pattern, by using the corresponding 3D SD-OCT volume data, and improved the reproducibility of TD-OCT RNFL thickness measurements in all sectors except global mean (Table 3). FIG. 11 shows that RNFBD model agrees well with localized defect due to glaucoma. This indicates that the multiple TD-OCT RNFL measurements from longitudinal repeated TD-OCT scans can be compared in ideally the same location, regardless the accuracy of the actual scan location (FIG. 5). In other words, the approach of the invention makes it possible for clinicians to track, compare, and detect any retinal changes over a longer period of time with relatively low measurement variation, which may enable more reliable and sensitive glaucomatous progression analysis.

With the present invention, RNFL thickness-measurement normalization effected by combining individual mathematical RNFBD models and the SLM algorithm improves the reproducibility of TD-OCT RNFL thickness measurements. In addition, the inventive methodology constitutes a useful tool for study of longitudinal glaucoma progression.

DETAILED DESCRIPTION OF THE PREFERRED EMBODIMENTS

Introduction

Optical coherence tomography, which was developed in 1991 by D. Huang, J. Schuman, et al at the Massachusetts Institute of Technology (MIT), Cambridge, is a low-coherence, interferometer-based, noninvasive medical imaging modality that can provide non-contact, real-time, high-resolution, cross-sectional images of biological tissue.[1] According to a new market research report (Optical Coherence Tomography—Technology, Markets and Applications: 2008-2012 published by US media company PennWell (Tulsa, Okla.)), the optical coherence tomography (OCT) market will grow with revenues expected to top $800 million by 2012. The report estimates that the global market for OCT systems currently stands at around $200 million and is growing at an annual rate of 34% (Medical Physics Web; Jan. 16, 2008; http://medicalphysicsweb.org/cws/article/research/32456). The first conventional time domain OCT (TD-OCT; Stratus OCT) was commercialized by Carl Zeiss Meditec, Inc. (CZMI), Dublin, Calif.

Glaucoma is the second leading cause of blindness worldwide. In order to diagnose and monitor the progression of glaucoma, ophthalmologists utilize: 1) functional assessment and 2) structural assessment.[2-4] Visual field (VF; Humphrey Visual Field Analyzer, HVF Ili, Carl Zeiss Meditec, Inc. (CZMI), Dublin, Calif.) testing can be performed to assess functional damage. In order to quantitatively assess structural changes, measurements of the retinal nerve fiber layer (RNFL) thickness and optic nerve head (ONH) are analyzed. Quantification of structural damage can be assessed by many different imaging modalities such as confocal scanning laser tomography (CSLT), scanning laser polarimetry (SLP), and OCT[5-7] TD-OCT has been widely accepted to quantitatively assess the RNFL.[8-10] Previous studies have shown that structural changes of both RNFL thickness and ONE shape can be early indicators for glaucomatous abnormality.[11] Many times glaucomatous progression by VF is detected only after significant RNFL loss has already occurred (FIG. 1).[12] RNFL measurements using repeated OCT scans at different time points (months or years) are needed to detect glaucoma progression, which can appear earlier than VF changes.[10]

Figure 2:
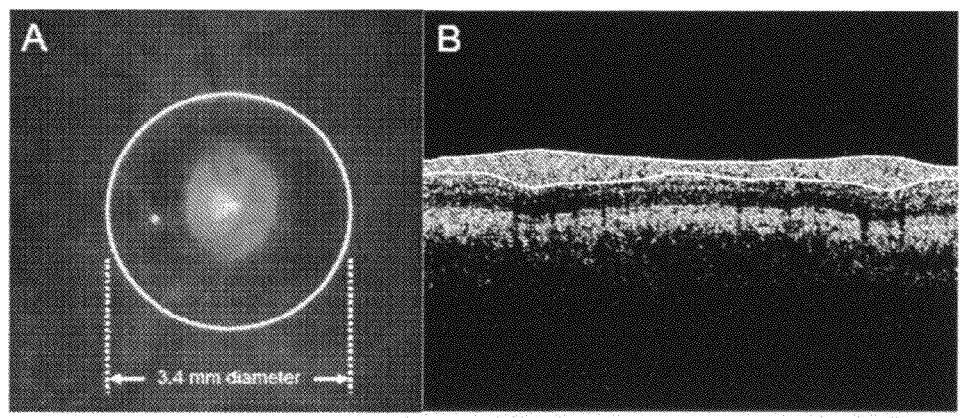
FIG. 2. Visualization of A) TD-OCT 3.4 mm diameter circle scan and B) its cross-sectional image and RNFL segmentation (light solid) along the circle in depth. Major vessel generates a shadow artifact (vertical dark lines on (B)) because scanning beam is absorbed by blood flow.
Figure 3:
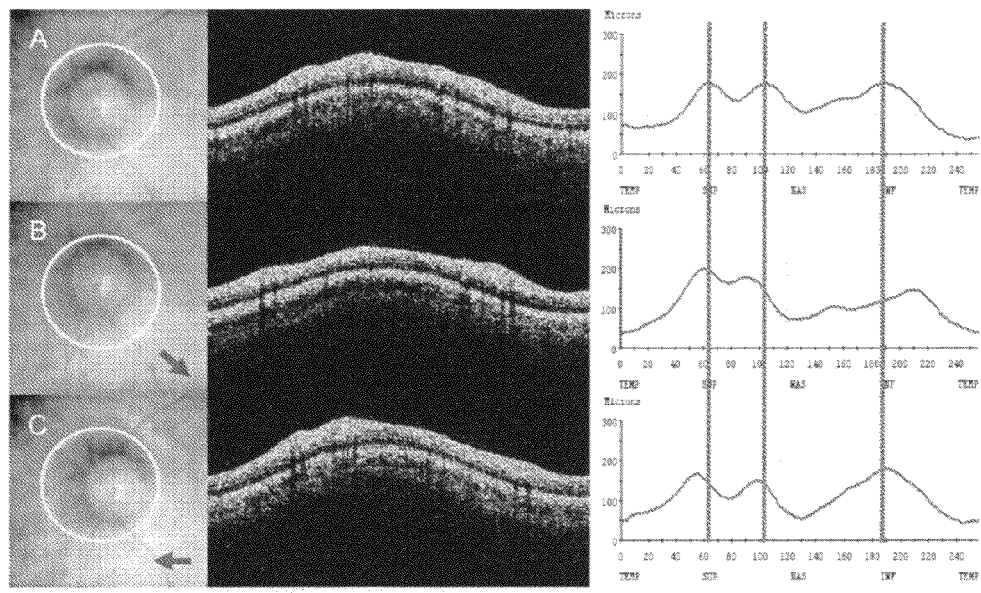
FIG. 3. A limitation of TD-OCT circular scan is illustrated: scanning location variation due to the manual placement of the scanning circles. A) a properly centered circle, B) the scanning circle was displaced inferior temporally, and C) the circle was displaced nasally. As a result of displacement, RNFL thickness profile graphs show peak location shifting and differences in RNFL thickness measurements.

RNFL thickness can be measured on a TD-OCT circle scan, which is a cross-sectional retinal image sampled along a 3.4 mm diameter circle and centered on the optic nerve head (ONH, FIG. 2). One limitation of TD-OCT circle scan is that the operator manually places the TD-OCT circle scan around the ONH. This introduces measurement variability and diminishes the accuracy and reliability of long term follow-up (FIG. 3).[13,14] There is a method (e.g. Repeat-scan function of Stratus OCT system software, CZMI) that improves the reliability of ONH circle scan. This function automatically places and normalizes the TD-OCT circle scan in the unique and universal location relative to the fixation target as it was in a previous (base-line) scan. Yet, the algorithm provides only a small improvement.[15]

Figure 4:
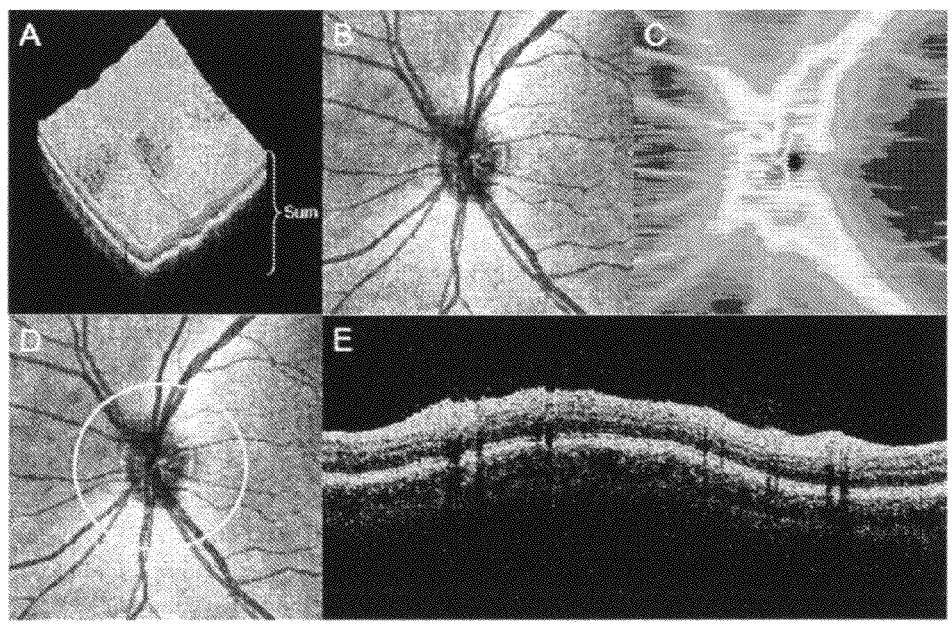
FIG. 4. 3D SD-OCT data visualization. By summing the reflectivity data in z-direction (A), OCT fundus (en face) image is generated (B). Two dimensional RNFL thickness map (C) can be created by segmenting RNFL on each B-scan of SD-OCT volume (raster) scan. On the OCT fundus image, one can specify any re-sampling path (e.g. circular scanning path shown on D) so that virtual re-sampled OCT cross-sectional image can be generated (E).

As noted above, SD-OCT technology has been introduced providing faster scanning (up to 100×) and finer axial resolution (up to 2×) compared to TD-OCT.[16] Faster scanning allows high resolution three-dimensional (3D) volume sampling by raster scanning in the region of interest. By summing the back scattered signal at each transverse point of a retinal raster scan (3D SD-OCT), data can be visualized as an en face image of the retina (FIG. 4). The en face retinal image is also known as an OCT fundus image (FIG. 4A).[17] The OCT fundus image permits the detection of eye movements during scanning by checking for discontinuities in retinal blood vessels. It also can be used to create a virtual OCT cross-sectional (B-scan) image along any sampling line (curved or straight) (FIG. 4B, circle). Therefore, near perfect registration of a virtually sampled B-scan image can be achieved. In addition, a two dimensional (2D) RNFL thickness map (FIG. 4C) can be created by segmenting RNFL on each B-scan of SD-OCT volume (raster) scan.

The present invention normalizes the RNFL thickness measurements of off-centered TD-OCT circle scans to a universal (virtual) location centered on the ONH of the same eye. Both a mathematical model of the retinal tissue pattern and a scan location matching (SLM) algorithm (PCT/US2009/052951) are used for this calculation.[18] Using the normalized RNFL thickness measurements avoids the previous downfall of RNFL thickness measurement variability. This makes it possible for clinicians to track, compare, and detect any retinal changes over a longer period of time.

Method

Anatomy of the Retina

Figure 1:
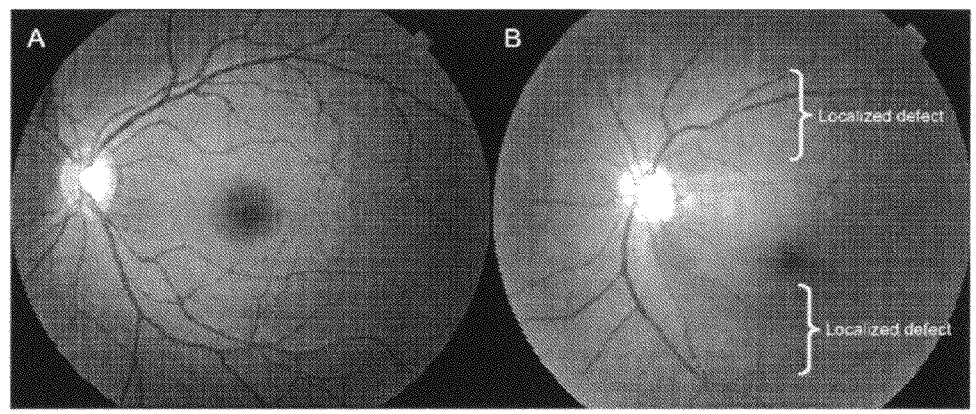
FIG. 1. Healthy eye A) and glaucomatous eye B) with localized wedge-shaped RNFL defect due to the presence of glaucomatous damage.
Figure 5:
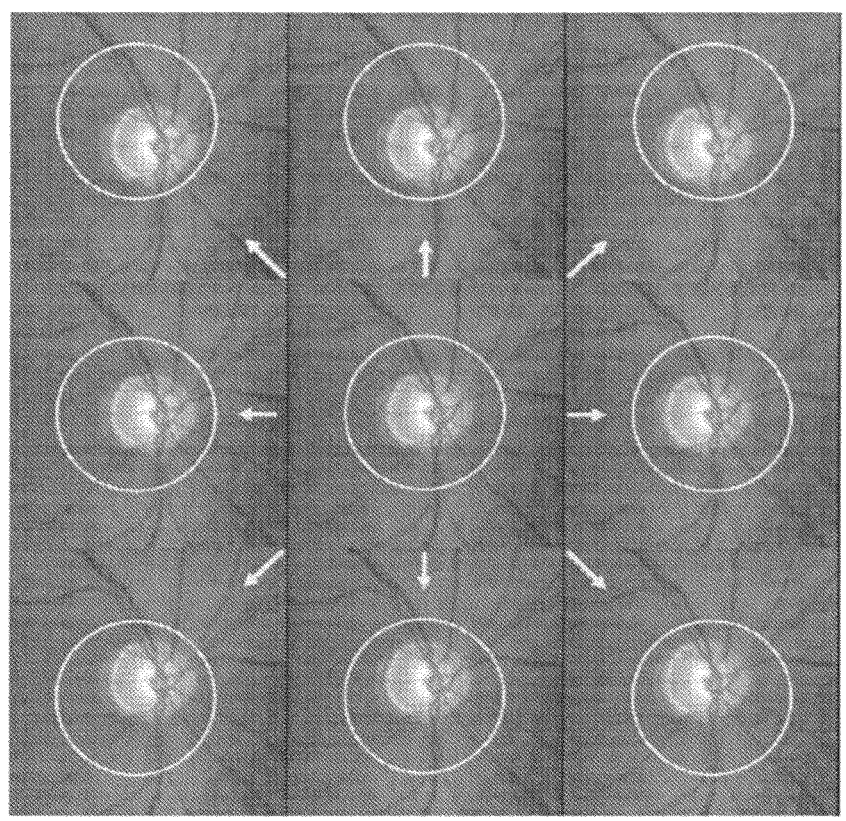
FIG. 5. Illustration of TD-OCT Circle scans in 9 different locations per eye.
Figure 6:
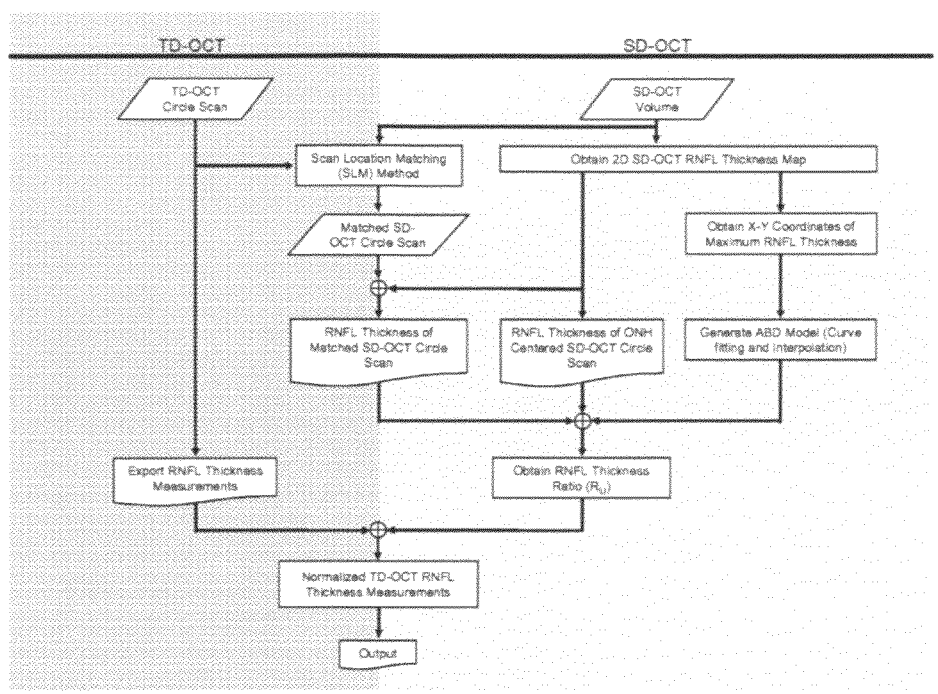
FIG. 6. Flow diagram of TD-OCT RNFL thickness measurement normalization process.

Glaucoma is a progressive optic neuropathy, which induces irreversible retinal ganglion cell loss and leads to characteristic patterns of vision loss. As mentioned above, structural changes are manifested by RNFL thinning due to axon loss (FIG. 5). According to Lepper et al., axons originate from the retinal ganglion cells and converge at the ONH. Glaucomatous damage occurs along the axon bundle, as FIG. 1 depicts. One of the major purposes of the TD-OCT circle scan is to detect this axon bundle loss around the ONH.

Mathematical Axon Bundle Distribution (ABD) Mapping and Normalization of RNFL Thickness Measurements SLM method itself is not enough for clinical application, especially in detecting glaucoma progression. RNFL measurements from multiple scans over time must be re-centered and normalized at a universal location. This allows the RNFL thickness measurements, which may change over time, to be directly compared without the inherent variation in TD-OCT scan registration. Normalizing circular scanned RNFL measurements can be achieved by combining the RNFL thickness profiles at the matched scan locations on SD-OCT fundus image and an ABD mathematical model of the retina.

This normalization can be achieved by combining the following:
1) A newly invented mathematical axon bundle distribution mapping (FIG. 7), which is a simplified version of anatomical axon bundle distribution pattern on the retina.
2) The 2D RNFL thickness map detected on the corresponding SD-OCT 3D volume data (FIG. 7B).
3) The SLM algorithm described in PCT/US2009/052951 (published as WO 2010/017356).

Figure 7:
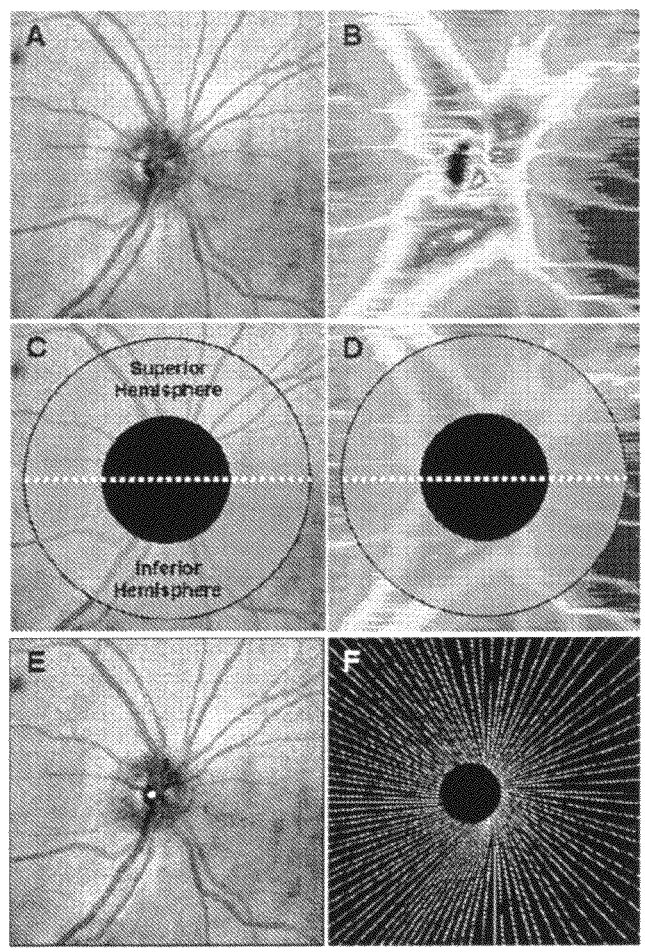
FIG. 7. Mathematical ABD mapping: A) 3D SD-OCT volume, B) 2D RNFL thickness map of SD-OCT volume, C) search boundary (region delineated by outer circle) for the center of RNFL thickness on SD-OCT fundus image, D) search boundary for the center of RNFL thickness on 2D RNFL thickness map, E) the computed centers, i.e., center of gravity light line), of RNFL thickness at each radius, F) RNFBD map derived after mathematical interpolation of two fitted curves (E, light lines).
Figure 8:
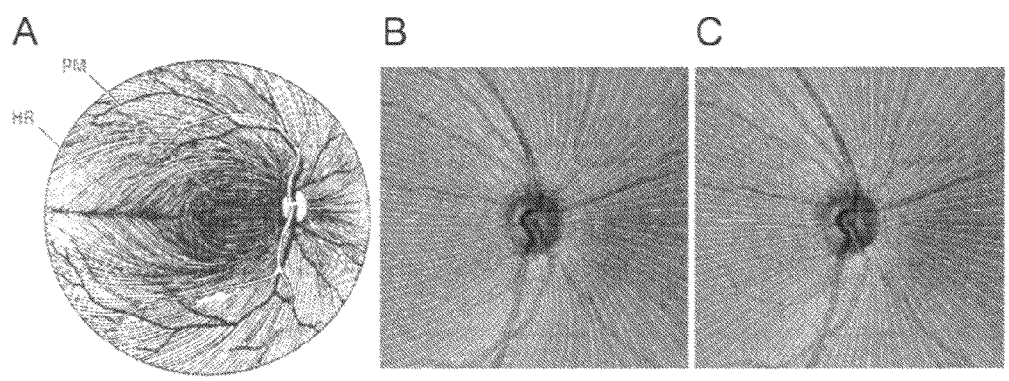
FIG. 8. Visualization of the two different mathematical RNFBD mapping methods: A) anatomical RNFBD pattern, B) quadratic RNFBD mapping method, and C) quasi-linear RNFBD mapping method. The curvature of each method is different (i.e., quadratic and linear).
Figure 9:
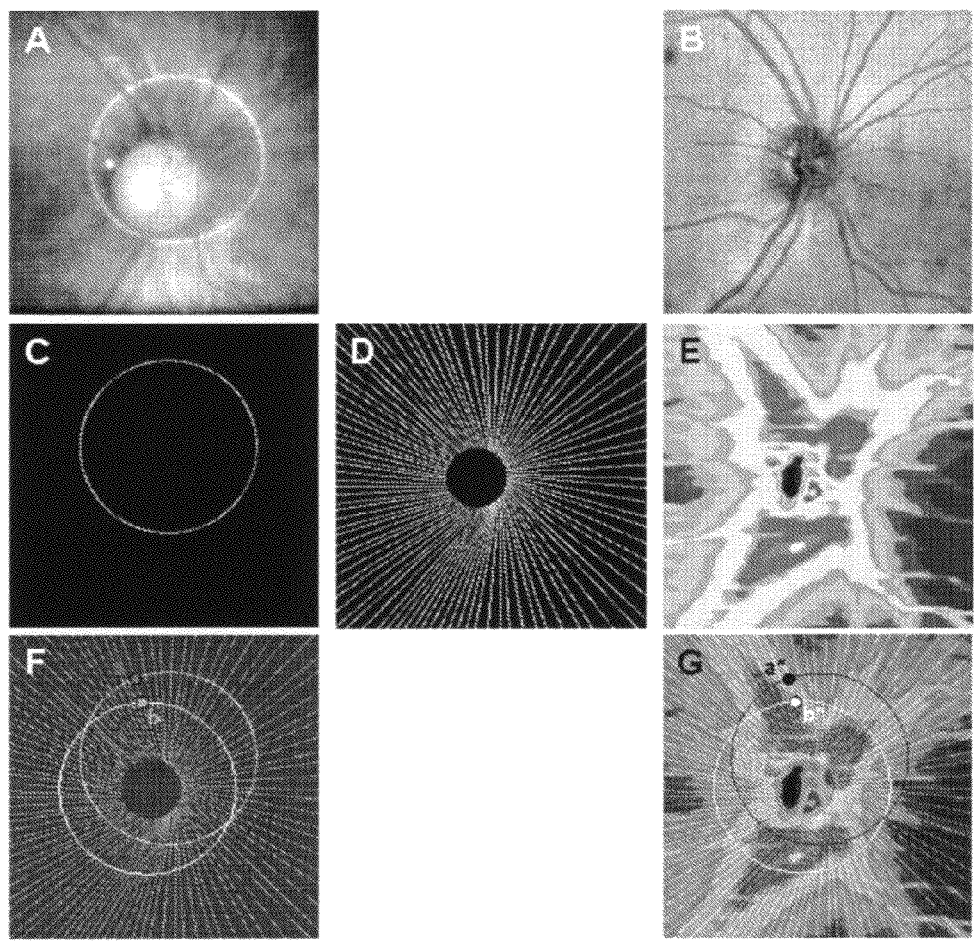
FIG. 9. Visualization of TD-OCT RNFL thickness measurement normalization process: A) TD-OCT circle scan, B) 3D SD-OCT cube scan, C) matched scan location within SD-OCT cube scan using SLM method and RNFL thickness of (A) in pseudo-color scale, D) axon bundle distribution map, E) 2D RNFL thickness map of (B), F) universal (virtual) location (circle b) in TD-OCT scale centered on the optic nerve head, G) universal location (circle b) in SD-OCT scale centered on the optic nerve head. RNFL thickness measurement of TD-OCT circle scan at the universal location (F, circle b) is computed by using the ratio (RU) between a/b=a*/b*.

FIGS. 7, 8, and 9 provide a visualization of normalization process of the off-centered TD-OCT RNFL thickness measurement. The following is the description of this process, with reference to FIG. 9:

1) Find TD-OCT circle scan location within SD-OCT volume by using SLM algorithm.
2) Obtain the RNFL thickness of TD-OCT circle scan.
3) Obtain 2D RNFL thickness map from SD-OCT volume scan.
4) Compute the center (i.e., center of gravity) of RNFL thickness of superior hemi-sphere and inferior hemi-sphere from three or more concentric circles.
5) Generate the n-th order polynomial functions based on the X-Y coordinates of the center of RNFL thickness of superior hemi-sphere and inferior hemi-sphere. For example, the current setup to estimate ABD is a second order polynomial (quadratic) function.
6) Perform a mathematical interpolation to fill in the missing curves between the two dotted lines (FIG. 7F, light lines). The number of curves to be interpolated can be adjusted by the user.
7) Obtain the RNFL thickness measurements along virtual axon bundle path (FIG. 7F, light lines) on the 2D SD-OCT RNFL thickness map.
8) Compute the normalized RNFL thickness measurements at the virtual location (FIGS. 9F and G, circle b) by the following:
   a) The RNFL thickness change along axon bundle path as a ratio (RU) will be computed by using SD-OCT RNFL thickness map.
   b) The RNFL thickness measurement (FIG. 9F, b) of TD-OCT scan at the virtual location will be computed by multiplying the RNFL thickness measurement (FIG. 9F, a) at the TD-OCT circle scan location and the RNFL thickness ratio (RU) from the 2D RNFL thickness map of SD-OCT volume.
   c) The TD-OCT RNFL thickness normalization equation is:

$$b(x,y)=a(x,y)*Ru,$$

$$Ru=b*(x,y)/a*(x,y),$$

a(x, y): RNFL thickness of the off-centered TD-OCT circle scan,
   b(x, y): RNFL thickness at the virtual location on TD-OCT scale,
   a*(x, y): RNFL thickness at the matched SD-OCT circle scan
   b*(x, y): RNFL thickness at the ONH centered SD-OCT circle scan,
   x, y: X-Y coordinate on the SD-OCT fundus image.
9) Export the normalized TD-OCT RNFL thickness measurement at the virtual location, which is a 3.4-mm diameter circle centered on the ONH (see FIG. 9).

Subject recruitment and inclusion criteria are discussed above. With respect to image acquisition, it is noted already that the peripapillary region was scanned on all eyes using TD-OCT (Stratus OCT; CZMI) and SD-OCT (Cirrus HD-OCT; CZMI) at a single visit.

Figure 10:
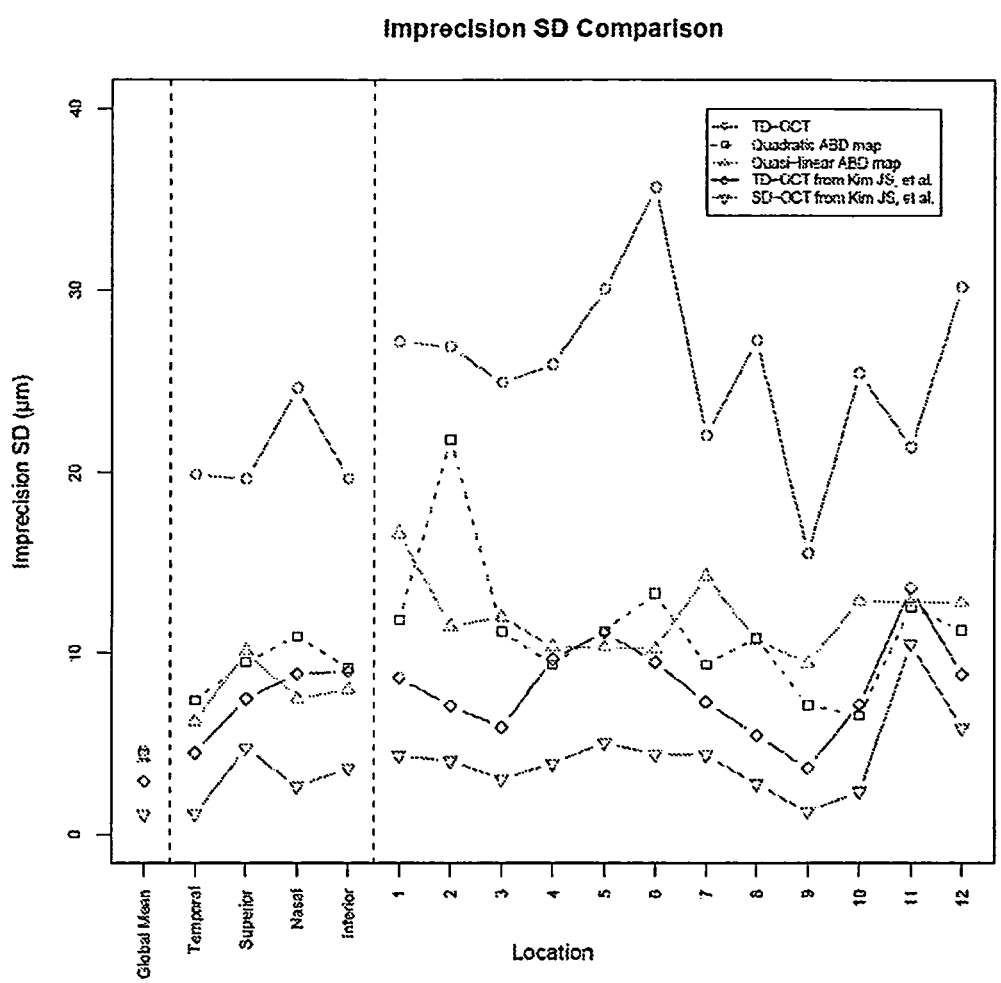
FIG. 10. The imprecision SD plot. The variability of normalized RNFL thickness measurements was statistically significantly lower than the actual TD-OCT circle scan except global mean. In addition, the variability of Kim et al. study[17] (dard solid) was plotted for comparison purpose.

As previously noted, circular scans centered on the ONH were obtained using the Circle Scan pattern, which was a single 3.4 mm diameter circular scan with 256*1024 samplings acquired in 0.64 second. Nine Circle scans were obtained from each eye in a single session by one operator. Each of 9 scans had its scanning circle manually centered differently (FIG. 10). Starting with the circle manually centered on the ONH followed by 8 different manual displacements so that each circle had clearly visible displacement without touching the ONH margin. Images with signal strength (SS) less than 6 were discarded as poor quality images as the manufacturer recommends. RNFL thickness was measured using the Stratus OCT system software version 5.0. Segmentation failure was defined as obvious deviation of the segmented inner and/or outer RNFL borders from the subjectively perceived borders. Consecutive 5% or cumulative 10% segmentation failure within a given image was considered to be poor analysis quality and discarded.

Figure 11:
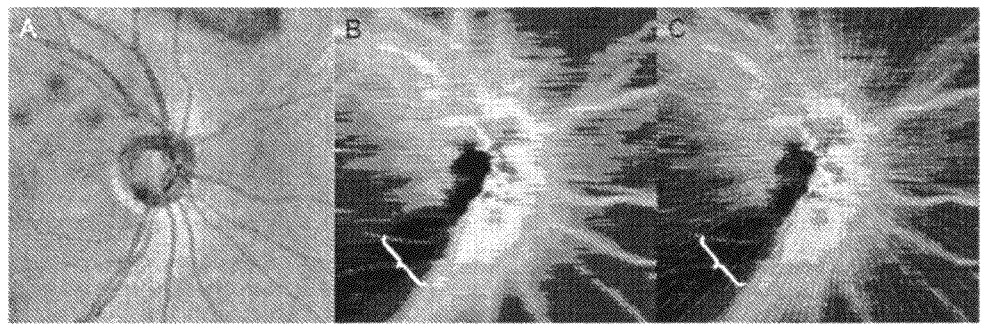
FIG. 11. RNFBD mapping sample: A) SD-OCT fundus image from a glaucomatous eye, B) 2D RNFL thickness map of SD-OCT from the same eye, and C) RNFBD map superimposed with (B). The RNFBD model agrees well with localized defect due to glaucoma.

Also as indicated above, a single Optic Disc Cube 200×200 scan was obtained from each eye (FIG. 11). This isotropic (equal A-scan spacing in X- and Y-plane) raster scan contained 200*200*1024 samplings of a 6*6*2 mm volume manually centered on the ONH, and was acquired in 1.48 seconds. Images with SS less than 8 were discarded as poor quality images, as the manufacturer recommends. This cutoff differs from that of TD-OCT because of inherent hardware and software differences between the two platforms. Inclusion also required that eye movements must be less than the diameter of major vessels judged on OCT fundus images. The segmentation quality criteria for virtual OCT slices (or re-sampled images) from the Cirrus scans was the same as for the Stratus OCT scans with the additional criteria of more than 10% of frames labeled as analysis failure disqualified any scan.

ABD Model Performance Assessment and Results

The performance of the RNFL thickness normalization method was assessed by comparing the standard deviation of the global and sectoral RNFL thickness measurements of both methods: 1) the actual TD-OCT scan and 2) the normalization. TD-OCT RNFL thickness measurements were obtained using StratusOCT software 5.0. SD-OCT RNFL thickness measurements were obtained using our own software. The virtual circle scan location (e.g., ONH centered 3.4-mm diameter circle) of TD-OCT circle scan was also obtained from this SD-OCT software. Paired t-test results (Table 1) of the average RNFL thickness measurement standard deviation between two methods showed that the difference was statistically significant for all sectors except global mean (p=0.06). This means that the present invention properly identifies anatomical retinal axon bundle distribution patterns and reduces TD-OCT RNFL thickness measurement variation caused by off-centered circle scan. For example, FIG. 11 shows that the normalized TD-OCT RNFL thickness measurements from the 9 different TD-OCT circle scans became more similar than the actual TD-OCT circle scans.

REFERENCES

1. Kline L B, Foroozan R. Optic nerve disorders. 2nd edition. Ophthalmology Monograph 10. American Academy of Ophthalmology. New York: Oxford University Press 2007.
2. Grehn F, Stamper R (eds). Glaucoma. (Essentials in Ophthalmology series). Springer, Berlin Heidelberg New York, 2004.
3. Huang D, Swanson E A, Lin C P, et al. Optical coherence tomography. Science 1991; 254:1178-81.
4. Schuman J S, Hee M R, Puliafito C A, et al. Quantification of nerve fiber layer thickness in normal and glaucomatous eyes using optical coherence tomography. Arch Ophthalmol 1995; 113:586-96.
5. Schuman J S, Hee M R, Arya A V, et al. Optical coherence tomography: a new tool for glaucoma diagnosis. Curr Opin Ophthalmol 1995; 6:89-95.
6. Wollstein G, Schuman J S, Price L L, et al. Optical coherence tomography longitudinal evaluation of retinal nerve fiber layer thickness in glaucoma. Arch Ophthalmol 2005; 123:464-70.
7. Cheung C Y, Yiu C K, Weinreb R N, et al. Effects of scan circle displacement in optical coherence tomography retinal nerve fibre layer thickness measurement: a RNFL modelling study. Eye 2009; 23:1436-41.
8. Gabriele M L, Ishikawa H, Wollstein G, et al. Optical coherence tomography scan circle location and mean retinal nerve fiber layer measurement variability. Invest Ophthalmol Vis Sci 2008; 49:2315-21.
9. Tzamalis A, Kynigopoulos M, Schlote T, et al. Improved reproducibility of retinal nerve fiber layer thickness measurements with the repeat-scan protocol using the Stratus OCT in normal and glaucomatous eyes. Graefes Arch Clin Exp Ophthalmol. 2009; 247:245-52.
10. Drexler W, Fujimoto J G. State-of-the-art retinal optical coherence tomography. Prog Retin Eye Res 2008; 27:45-88.
11. Wojtkowski M, Bajraszewski T, Gorczynska I, et al. Ophthalmic imaging by spectral optical coherence tomography. Am J Ophthalmol 2004; 138:412-9.
12. Wojtkowski M, Srinivasan V, Fujimoto J G, et al. Three-dimensional retinal imaging with high-speed ultrahigh-resolution optical coherence tomography. Ophthalmology 2005; 112:1734-46.
13. Srinivasan V J, Adler D C, Chen Y, et al. Ultrahigh-speed optical coherence tomography for three-dimensional and en face imaging of the retina and optic nerve head. Invest Ophthalmol Vis Sci 2008; 49:5103-10.
14. Kim J S, Ishikawa H, Wollstein G, et al. Retinal Nerve Fiber Layer Thickness Measurement Comparability between Time Domain Optical Coherence Tomography (OCT) and Spectral Domain OCT, Invest Ophthalmol Vis Sci 2009; Accepted.
15. Mumcuoglu T, Wollstein G, Wojtkowski M, et al. Improved visualization of glaucomatous retinal damage using high-speed ultrahigh-resolution optical coherence tomography. Ophthalmology 2008; 115:782-9.
16. Atkinson K E. An introduction to numerical analysis. Second Edition. John Wiley & Sons, Inc. 1989.
17. Kim J S, Ishikawa H, Sung K R, et al. Retinal Nerve Fiber Layer Thickness Measurement Reproducibility Improved with Spectral Domain Optical Coherence Tomography. Br J Ophthalmol, 2009. [Epub ahead of print]

What is claimed is:

1. A method of normalizing thickness measurements of a retinal nerve fiber layer in a two-dimensional optical coherence tomography image and a three-dimensional optical coherence tomography image, each image containing said layer comprising the steps of:
   (A) performing at least one circle scan in said two-dimensional image to obtain a thickness of said layer;
   (B) establishing image registration between said two-dimensional image and said three-dimensional image;
   (C) generating a two-dimensional thickness map of said thickness of said layer from said three-dimensional image;
   (D) performing at least three concentric circle scans for each of the superior hemi-sphere and the inferior hemi-sphere of said layer in said two-dimensional thickness map to delineate space coordinates of a center of gravity of said thickness in each respective hemi-sphere;
   (E) generating at least one polynomial function based on said space coordinates of said respective centers of gravity to create a plurality of fitting curves; and
   (F) performing a mathematic interpolation of said plurality to obtain thickness measurements along a virtual path in said two-dimensional thickness map, whereby said thickness measurements of said layer are normalized along said virtual path.

2. The method of claim 1, wherein said polynomial function is a second order polynomial function.

\* \* \* \* \*

UNITED STATES PATENT AND TRADEMARK OFFICE
CERTIFICATE OF CORRECTION

| | |
|---|---|
| PATENT NO. | : 8,911,089 B2 |
| APPLICATION NO. | : 13/510732 |
| DATED | : December 16, 2014 |
| INVENTOR(S) | : Jong S. Kim et al. |

Page 1 of 1

It is certified that error appears in the above-identified patent and that said Letters Patent is hereby corrected as shown below:

In the Specification

In Column 1, Lines 17-23, replace:
"This invention was made with United States government support in part under grant numbers R01-EY13178-09, ROI-EY11289-23, and P30-EY08098-20, awarded by the National Institutes of Health (Bethesda, MD), The Eye and Ear Foundation (Pittsburgh, PA), and unrestricted grants from Research to Prevent Blindness, Inc. (New York, NY). The United States government has certain rights in the invention."

With the following:
--This invention was made with United States government support under grant numbers EY013178, EY011289, and EY008098 awarded by the National Institutes of Health. The United States government has certain rights in the invention.--

Signed and Sealed this
First Day of January, 2019

Andrei Iancu
*Director of the United States Patent and Trademark Office*